US008283124B2

(12) United States Patent
Birkenmeyer et al.

(10) Patent No.: US 8,283,124 B2
(45) Date of Patent: Oct. 9, 2012

(54) **COMPOSITIONS FOR DETECTING ANTIBODIES TO *BABESIA MICROTI* AND METHODS OF USES THEREOF**

(75) Inventors: Larry G. Birkenmeyer, Glenview, IL (US); Suresh M. Desai, Libertyville, IL (US); Dinesh O. Shah, Libertyville, IL (US); Yu Cheng, Mundelein, IL (US); George J. Dawson, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 365 days.

(21) Appl. No.: 11/924,131

(22) Filed: Oct. 25, 2007

(65) Prior Publication Data
US 2009/0111123 A1    Apr. 30, 2009

(51) Int. Cl.
*G01N 33/53* (2006.01)
(52) U.S. Cl. ..................................... 435/7.1
(58) Field of Classification Search ................ None
See application file for complete search history.

(56) References Cited

U.S. PATENT DOCUMENTS

| | | | |
|---|---|---|---|
| 5,006,309 | A | 4/1991 | Khalil et al. |
| 5,063,081 | A | 11/1991 | Cozzette et al. |
| 5,089,424 | A | 2/1992 | Khalil et al. |
| 6,183,976 | B1 | 2/2001 | Reed et al. |
| 6,214,971 | B1 | 4/2001 | Reed et al. |
| 6,306,396 | B1 | 10/2001 | Reed et al. |
| 6,451,315 | B1 | 9/2002 | Reed et al. |
| 6,569,433 | B1 | 5/2003 | Reed et al. |
| 2003/0109689 | A1* | 6/2003 | Reed et al. .......... 536/23.1 |
| 2003/0170881 | A1 | 9/2003 | Davis et al. |
| 2004/0018577 | A1 | 1/2004 | Emerson Campbell et al. |
| 2004/0023865 | A1 | 2/2004 | Reed et al. |
| 2005/0054078 | A1 | 3/2005 | Miller et al. |
| 2006/0160164 | A1 | 7/2006 | Miller et al. |

FOREIGN PATENT DOCUMENTS

| | | |
|---|---|---|
| EP | 834567 A2 | 4/1998 |
| WO | WO 0185947 A2 * | 11/2001 |
| WO | WO02053016 A2 | 7/2002 |

OTHER PUBLICATIONS

Anderson, J.F. & Magnarelli, L.A., "Babesiosis in Fairfield County, Connecticut", Emerg. Inf. Dis., 10(3):545-560 (2004).
Arai, S., et al., "Retrospective Seroepidemiological Survey for Human Babesiosis in an Area in Japan Where a Tick-Borne Disease is Endemic", J. of Veterinary Med. Sci., 65(3):335-340 (2003).
Barnes, D., et al. "Serum-Free Cell Culture: a Unifying Approach", Cell, 22:649-655 (1980).
Cable, R.G. & Leiby, D.A., "Risk and prevention of transfusion-transmitted babesiosis and other tick-borne diseases", Current Opin. in Hematology, 10:405-411 (2003).
Cohen, S.N., et al., "Nonchromosomal Antibiotic Resistance in Bacteria: Genetic Transformation of *Escherichia coli* by R-Factor DNA", Proc. Natl. Acad. Sci. USA, 69(8):2110-2114 (1972).
Dobroszycki, J., et al., "A Cluster of Transfusion-Associated Babesiosis Cases Traced to a Single Asymptomatic Donor", JAMA, 281(10:927-930 (1999).
Feder, Jr., H.M., "Babesiosis in Pregnancy", New Engl. J. of Med., 349(2):195-196 (2003).
Gorman, C.M., et al., "Transient Production of Proteins Using an Adenovirus Transformed Cell Line", DNA and Prot. Eng. Tech., 2(1):3-10 (1990).
Graham, F.L. & Van Der Eb, A.J., "A New Technique for the Assay of Infectivity of Human Adenovirus 5 DNA", Virology, 52:456-467 (1973).
Haugland, R.P., "Handbook of Fluorescent Probes and Research Chemicals", 6th Ed., TOC, 1996.
Henaut, A. & Danchin, A., "Analysis and Predictions from *Escherichia coli* Sequences, or *E. coli* in Silico", Analysis and Pred. from *Escherichia coli* Seq., Chapt. 114, 2047-2066 (1966).
Herwaldt, B.L., "Babesiosis in Wisconsin: A Potentially Fatal Disease", Am. J. Trop. Med. Hyg., 53(2):146-151 (1995).
Herwaldt, B.L., et al., "Endemic Babesiosis in Another Eastern State: New Jersey", Emerg. Inf. Dis., 9(2):184-188 (2003).
Herwaldt, B.L., et al., "Babesia divergens-like Infection, Washington State", Emerg. Inf. Dis., 10(4):622-629 (2004).
Hinnen, A., et al., "Transformation of yeast", Proc. Natl. Acad. Sci. USA, 75(4)-1929-1933 (1978).
Homer, M.J., et al., "A Polymorphic Multigene Family Encoding an Immunodominant Protein from *Babesia microti*", J. of Clin. Microbiol., 38(1):362-368 (2000).
Homer, M.J., et al., "Babesiosis", Clin. Microbiol. Rev., 13(3):451-469 (2000).
Homer, M. J., et al., "Identification and Characterization of Putative Secreted Antigens from *Babesia microti*", J. of Clin. Microbiol., 41(2):723-729 (2003).
Houghton, R.L., et al., "Identification of *Babesia microti*-specific immunodominant epitopes and development of a peptide EIA for detection of antibodies in serum”, Transfusion, 42:1488-1496 (2002).

Kjemtrup, A.M. & Conrad, P.A., “Human babesiosis: an emerging tick-borne disease”, Intnl. J. for Parasitology, 30:1323-1337 (2000).

Kogut, S.J., et al., “*Babesia microti*, Upstate New York”, Emerg. Inf. Dis., 11(3):476-478 (2005).

Krause, P.J., et al., “Disease-Specific Diagnosis of Coinfecting Tickborne Zoonoses: Babesiosis, Human granulocytic Ehrlichiosis, and Lyme Disease”, Clin. Inf. Dis., 34:1184-1191 (2002).

Krause, P.J., et al., “Increasing Health Burden of Human Babesiosis in Endemic Sites”, Am. J. Trop. Med. Hyug., 68 (4):431-436 (2003).

Krause, P.J., “Babesiosis Diagnosis and Treatment, Vector-Borne and Zoonotic Diseases”, 3(1):45-51 (2003).

Leiby, D.A., et al. “Demonstrable parasitemia among Connecticut blood donors with antibodies to *Babesia microti*”, Transfusion, 45:1804-1810 (2005).

Linden, J.V., et al., “Transfusion-associated transmission of babesiosis in New York State”, Transfusion, 40 (3):285-289 (2000).

(Continued)

*Primary Examiner* — Brian J Gangle
(74) *Attorney, Agent, or Firm* — Cheryl L. Becker

(57) ABSTRACT

The present invention relates to one or more peptides which may be used to test for the presence of antibodies to *B. microti*. These peptide are selected based on the strength and specificity of the human antibody response to *B. microti*. These peptides alone or in combination have a variety of uses, for example, as a component of a diagnostic assay or kit.

11 Claims, 2 Drawing Sheets

OTHER PUBLICATIONS

Loa, C. C., et al., "Serological Diagnosis of Human Babesiosis by IgG Enzyme-Linked Immunosorbent Assay", Curr. Microbiol., 49:385-389 (2004).

Lodes, M.J., et al., "Secrological Expression Cloning of Novel Immunoreactive Antigens of *Babesia microti*", Inf. and Immun., 68(5):2783-2790 (2000).

"Mammalian Cell Biotechnology—A Practical Apporach", TOC (1991).

"Mammalian Cell Culture—The Use of Serum-Free Hormone-Supplemented Media", TOC (1984).

McQuiston, J.H., et al., "Transmission of tick-borne agents of disease by blood transfusion: a review of known and potential risks in the United States", Transfusion, 40:274-284 (2000).

Meer-Scherrer, L., et al., "*Babesia microti* Infection in Europe", Curr. Microbiol., 48:435-437 (2004).

Piccaluga, P.P., et al., "Clinical Picture—Babesia infection in Italy", The Lancet Infectious Diseases, 4(4):212 (2004).

Polak, Introduction to Immunocytochemistry, 2nd Ed., TOC (1997).

Sackett, D.L., et al., "Clinical Epidemiology: A Basic Sci. for Clin. Medicine", 106-107 (1985).

Setty, S., et al., "Babesiosis—Two Atypical Cases From Minnesota and a Review", Am. J. Clin. Pathol., 120:554-559 (2003).

Sherr, V.T., "Human babesiosis—an unrecorded reality Absence of formal registry undermines its detection, diagnosis and treatment, suggesting need for immediate mandatory reporting", Medical Hypotheses, 63:609-614 (2004).

The Medical Letter on Drugs & Therapeutics, 34(865):17-26 (1992).

Anandarao R., et al., "Recombinant Multiepitope Protein for Early Detection of Dengue Infections," Clinical and Vaccine Immunology, 2006, vol. 13 (1), pp. 59-67.

Duzgun A., et al., "An ELISA for the Diagnosis of *Babesia ovis* Infection Utilizing a Synthetic, *Babesia bovis*-derived Antigen," Veterinary Parasitology, 1991, vol. 39 (3-4), pp. 225-231.

Huang X., et al., "Evaluation of Enzyme-Linked Immunosorbent Assays with Recombinant Antigens for the Serodiagnosis of equine Babesia Infections," Veterinary Parasitology, 2006, vol. 140 (1-2), pp. 158-161.

Huang X., et al., "Immunochromatographic Test for Simultaneous Serodiagnosis of *Babesia Caballi* and *B. equi* Infections in Horses," Clinical and Vaccine Immunology, 2006, vol. 13 (5), pp. 553-555.

International Search Report for Application No. PCT/US2008/080700, mailed on Mar. 30, 2009, 4 pages.

Landini M.P., et al., "Recombinant Mono- and Polyantigens to Detect Cytomegalovirus-Specific Immunoglobulin M in Human Sera by Enzyme Immunoassay," Journal of Clinical Microbiology, 1995, vol. 33 (10), pp. 2535-2542.

Ripalti A., et al., "Construction of Polyepitope Fusion Antigens of Human Cytomegalovirus ppUL32: Reactivity with Human Antibodies," Journal of Clinical Microbiology, 1994, vol. 32 (2), pp. 358-363.

Vornhagen R., et al., "IgM-Specific Serodiagnosis of Acute Human Cytomegalovirus Infection Using Recombinant Autologous Fusion Proteins," Journal of Virological Methods, 1996, vol. 60 (1), pp. 73-80.

\* cited by examiner

SEQUENCE LISTING

<160> NUMBER OF SEQ ID NOS: 16

<210> SEQ ID NO 1
<211> LENGTH: 519
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1

```
ggcaaaccga acaccaacaa atctgaaaaa gctgaacgca agtcccatga cacccagacc    60
acccaagaaa tctgtgaagc tggcatcaaa agctacgata ctcagactcc gcaagaaacc   120
tccgacgcgc acgaagaaga acacggtaac ctgaacaaaa acaaaagcgg taaagcgggc   180
attaaatctc ataacaccca gactccgctg aaaaaaaag gtggcacctg tgcgaacacc   240
aaattcgaag ctctgaacga cctgatcatt agcgactgcg agaaaaaagg cattaagatt   300
aacggcgcgt acatcgttgg cgcgggtgtg gaagctgtga ccgtgtctgt ttctgcgacc   360
tctaacggca ccgaatctgg tggtgcaggc agcggtactg gcacttccgt gtctgcaacc   420
agcaccctga ctggcaacgg tggcgaagcg ggcggcacca gcggcactac tacttcttct   480
ggcgcggctt ccggcaaagc tggcactggc actgcaggc                          519
```

<210> SEQ ID NO 2
<211> LENGTH: 173
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

```
Gly Lys Pro Asn Thr Asn Lys Ser Glu Lys Ala Glu Arg Lys Ser His
 1               5                  10                  15

Asp Thr Gln Thr Thr Gln Glu Ile Cys Glu Ala Gly Ile Lys Ser Tyr
                20                  25                  30

Asp Thr Gln Thr Pro Gln Glu Thr Ser Asp Ala His Glu Glu His
        35                  40                  45

Gly Asn Leu Asn Lys Asn Lys Ser Gly Lys Ala Gly Ile Lys Ser His
     50                  55                  60

Asn Thr Gln Thr Pro Leu Lys Lys Lys Gly Gly Thr Cys Ala Asn Thr
 65                  70                  75                  80

Lys Phe Glu Ala Leu Asn Asp Leu Ile Ile Ser Asp Cys Glu Lys Lys
                 85                  90                  95

Gly Ile Lys Ile Asn Gly Ala Tyr Ile Val Gly Ala Gly Val Glu Ala
                100                 105                 110

Val Thr Val Ser Val Ser Ala Thr Ser Asn Gly Thr Glu Ser Gly Gly
            115                 120                 125

Ala Gly Ser Gly Thr Gly Thr Ser Val Ser Ala Thr Ser Thr Leu Thr
        130                 135                 140

Gly Asn Gly Gly Glu Ala Gly Gly Thr Ser Gly Thr Thr Thr Ser Ser
145                 150                 155                 160

Gly Ala Ala Ser Gly Lys Ala Gly Thr Gly Thr Ala Gly
                165                 170
```

<210> SEQ ID NO 3
<211> LENGTH: 556
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (2)..(547)

<400> SEQUENCE: 3

```
g aat tcc atg ggc aaa ccg aac acc aac aaa tct gaa aaa gct gaa cgc        49
  Asn Ser Met Gly Lys Pro Asn Thr Asn Lys Ser Glu Lys Ala Glu Arg
   1               5                  10                  15 aag tcc cat gac acc cag acc acc caa gaa atc tgt gaa gct ggc atc          97
Lys Ser His Asp Thr Gln Thr Thr Gln Glu Ile Cys Glu Ala Gly Ile
             20                  25                  30 aaa agc tac gat act cag act ccg caa gaa acc tcc gac gcg cac gaa         145
Lys Ser Tyr Asp Thr Gln Thr Pro Gln Glu Thr Ser Asp Ala His Glu
         35                  40                  45 gaa gaa cac ggt aac ctg aac aaa aac aaa agc ggt aaa gcg ggc att         193
Glu Glu His Gly Asn Leu Asn Lys Asn Lys Ser Gly Lys Ala Gly Ile
     50                  55                  60 aaa tct cat aac acc cag act ccg ctg aaa aaa aaa ggt ggc acc tgt         241
Lys Ser His Asn Thr Gln Thr Pro Leu Lys Lys Lys Gly Gly Thr Cys
 65                  70                  75                  80 gcg aac acc aaa ttc gaa gct ctg aac gac ctg atc att agc gac tgc         289
Ala Asn Thr Lys Phe Glu Ala Leu Asn Asp Leu Ile Ile Ser Asp Cys
                 85                  90                  95 gag aaa aaa ggc att aag att aac ggc gcg tac atc gtt ggc gcg ggt         337
Glu Lys Lys Gly Ile Lys Ile Asn Gly Ala Tyr Ile Val Gly Ala Gly
             100                 105                 110 gtg gaa gct gtg acc gtg tct gtt tct gcg acc tct aac ggc acc gaa         385
Val Glu Ala Val Thr Val Ser Val Ser Ala Thr Ser Asn Gly Thr Glu
         115                 120                 125 tct ggt ggt gca ggc agc ggt act ggc act tcc gtg tct gca acc agc         433
Ser Gly Gly Ala Gly Ser Gly Thr Gly Thr Ser Val Ser Ala Thr Ser
     130                 135                 140 acc ctg act ggc aac ggt ggc gaa gcg ggc ggc acc agc ggc act act         481
Thr Leu Thr Gly Asn Gly Gly Glu Ala Gly Gly Thr Ser Gly Thr Thr
145                 150                 155                 160 act tct tct ggc gcg gct tcc ggc aaa gct ggc act ggc act gca ggc         529
Thr Ser Ser Gly Ala Ala Ser Gly Lys Ala Gly Thr Gly Thr Ala Gly
                 165                 170                 175 cat cat cac cat cac cat tgaggatcc                                       556
His His His His His His
             180
```

<210> SEQ ID NO 4
<211> LENGTH: 182
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

```
Asn Ser Met Gly Lys Pro Asn Thr Asn Lys Ser Glu Lys Ala Glu Arg
 1               5                  10                  15

Lys Ser His Asp Thr Gln Thr Thr Gln Glu Ile Cys Glu Ala Gly Ile
             20                  25                  30

Lys Ser Tyr Asp Thr Gln Thr Pro Gln Glu Thr Ser Asp Ala His Glu
         35                  40                  45

Glu Glu His Gly Asn Leu Asn Lys Asn Lys Ser Gly Lys Ala Gly Ile
     50                  55                  60

Lys Ser His Asn Thr Gln Thr Pro Leu Lys Lys Lys Gly Gly Thr Cys
 65                  70                  75                  80

Ala Asn Thr Lys Phe Glu Ala Leu Asn Asp Leu Ile Ile Ser Asp Cys
                 85                  90                  95
```

```
Glu Lys Lys Gly Ile Lys Ile Asn Gly Ala Tyr Ile Val Gly Ala Gly
            100                 105                 110

Val Glu Ala Val Thr Val Ser Val Ala Thr Ser Asn Gly Thr Glu
        115                 120                 125

Ser Gly Gly Ala Gly Ser Gly Thr Gly Thr Ser Val Ser Ala Thr Ser
130                 135                 140

Thr Leu Thr Gly Asn Gly Gly Glu Ala Gly Gly Thr Ser Gly Thr Thr
145                 150                 155                 160

Thr Ser Ser Gly Ala Ala Ser Gly Lys Ala Gly Thr Gly Thr Ala Gly
                165                 170                 175

His His His His His His
        180

<210> SEQ ID NO 5
<211> LENGTH: 26
<212> TYPE: PRT
<213> ORGANISM: Babesia microti

<400> SEQUENCE: 5

Gly Lys Pro Asn Thr Asn Lys Ser Glu Lys Ala Glu Arg Lys Ser His
1               5                   10                  15

Asp Thr Gln Thr Thr Gln Glu Ile Cys Glu
            20                  25

<210> SEQ ID NO 6
<211> LENGTH: 25
<212> TYPE: PRT
<213> ORGANISM: Babesia microti

<400> SEQUENCE: 6

Ile Lys Ser Tyr Asp Thr Gln Thr Pro Gln Thr Ser Asp Ala His
1               5                   10                  15

Glu Glu Glu His Gly Asn Leu Asn Lys
            20                  25

<210> SEQ ID NO 7
<211> LENGTH: 25
<212> TYPE: PRT
<213> ORGANISM: Babesia microti

<400> SEQUENCE: 7

Gly Asn Leu Asn Lys Asn Lys Ser Gly Lys Ala Gly Ile Lys Ser His
1               5                   10                  15

Asn Thr Gln Thr Pro Leu Lys Lys Lys
            20                  25

<210> SEQ ID NO 8
<211> LENGTH: 26
<212> TYPE: PRT
<213> ORGANISM: Babesia microti

<400> SEQUENCE: 8

Thr Cys Ala Asn Thr Lys Phe Glu Ala Leu Asn Asp Leu Ile Ile Ser
1               5                   10                  15

Asp Cys Glu Lys Lys Gly Ile Lys Ile Asn
            20                  25

<210> SEQ ID NO 9
<211> LENGTH: 25
<212> TYPE: PRT
<213> ORGANISM: Babesia microti
```

-continued

```
<400> SEQUENCE: 9

Tyr Ile Val Gly Ala Gly Val Glu Ala Val Thr Val Ser Val Ser Ala
 1               5                  10                  15

Thr Ser Asn Gly Thr Glu Ser Gly Gly
            20                  25

<210> SEQ ID NO 10
<211> LENGTH: 25
<212> TYPE: PRT
<213> ORGANISM: Babesia microti

<400> SEQUENCE: 10

Thr Glu Ser Gly Gly Ala Gly Ser Gly Thr Gly Thr Ser Val Ser Ala
 1               5                  10                  15

Thr Ser Thr Leu Thr Gly Asn Gly Gly
            20                  25

<210> SEQ ID NO 11
<211> LENGTH: 25
<212> TYPE: PRT
<213> ORGANISM: Babesia microti

<400> SEQUENCE: 11

Glu Ala Gly Gly Thr Ser Gly Thr Thr Thr Ser Ser Gly Ala Ala Ser
 1               5                  10                  15

Gly Lys Ala Gly Thr Gly Thr Ala Gly
            20                  25

<210> SEQ ID NO 12
<211> LENGTH: 51
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Gly Lys Pro Asn Thr Asn Lys Ser Glu Lys Ala Glu Arg Lys Ser His
 1               5                  10                  15

Asp Thr Gln Thr Thr Gln Glu Ile Cys Glu Glu Ala Gly Gly Thr Ser
            20                  25                  30

Gly Thr Thr Thr Ser Ser Gly Ala Ala Ser Gly Lys Ala Gly Thr Gly
        35                  40                  45

Thr Ala Gly
    50

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 13

His His His His His His
 1               5

<210> SEQ ID NO 14
<211> LENGTH: 5
<212> TYPE: PRT
<213> ORGANISM: Babesia microti
```

```
<400> SEQUENCE: 14

Gly Asn Leu Asn Lys
  1               5

<210> SEQ ID NO 15
<211> LENGTH: 5
<212> TYPE: PRT
<213> ORGANISM: Babesia microti

<400> SEQUENCE: 15

Thr Glu Ser Gly Gly
  1               5

<210> SEQ ID NO 16
<211> LENGTH: 556
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 16
ggatcctcaa tggtgatggt gatgatggcc tgcagtgcca gtgccagctt tgccggaagc      60
cgcgccagaa gaagtagtag tgccgctggt gccgcccgct tcgccaccgt tgccagtcag     120
ggtgctggtt gcagacacgg aagtgccagt accgctgcct gcaccaccag attcggtgcc     180
gttagaggtc gcagaaacag acacggtcac agcttccaca cccgcgccaa cgatgtacgc     240
gccgttaatc ttaatgcctt ttttctcgca gtcgctaatg atcaggtcgt tcagagcttc     300
gaatttggtg ttcgcacagg tgccacctttt tttttcagc ggagtctggg tgttatgaga     360
tttaatgccc gctttaccgc ttttgttttt gttcaggtta ccgtgttctt cttcgtgcgc     420
gtcggaggtt tcttgcggag tctgagtatc gtagcttttg atgccagctt cacagatttc     480
ttgggtggtc tgggtgtcat gggacttgcg ttcagctttt tcagatttgt tggtgttcgg     540
tttgcccatg gaattc                                                     556
```

COMPOSITIONS FOR DETECTING ANTIBODIES TO *BABESIA MICROTI* AND METHODS OF USES THEREOF

FIELD OF INVENTION

The present invention relates to compositions for identifying the presence of antibodies to parasite *Babesia microti* (*B. microti*), and assays and kits diagnosing the same.

BACKGROUND

*B. microti* is a tick-borne parasite that resides in the red blood cells of infected individuals causing a malarial-like sickness called babesiosis (Homer et al., *Clin. Microbiol. Rev.* 13(3):451-469 (2000)). *B. microti* is a potential risk to the blood supply as it can be transmitted to humans by the bite of infected ticks, but can also be transmitted by transfusion from infected blood donors to recipients of blood or blood products (Setty et al., *Am. J. Clin. Pathol.* 120:554-559 (2003)). Infection with *B. microti* represents one of the most common parasitic infections worldwide among wild and domestic animals, and humans (Homer et al., supra). The number of reported cases of *B. microti* infection in United States is increasing rapidly, particularly in the Northeast coastal states and the upper Midwest (Krause et al., *Am. J. Trop. Med. Hyg.* 68(4):431-436 (2003); Herwaldt et al., *Am. J. Trop. Med. Hyg.* 53(2):146-51 (1995)). Seroprevalence estimates of *B. microti* among blood donors range from 0.3% in Wisconsin donors to 4.3% in Shelter Island, N.Y. (Cable et al., *Current Opinion in Hematology* 10(6):405-411 (2003)).

Infection with *B. microti* often includes co-infection with lyme disease (Krause et al., *Clinical Infectious Diseases* 34:1184-1191 (2002)) and often remains undetected for extended periods of time. Babesiosis is potentially fatal, particularly in the elderly and in patients with suppressed immune systems (Kjemtrup et al., *Int. J. Parasitol* 30:1323-1337 (2000)). Patients infected with babesiosis and/or lyme disease share the same symptoms of muscle aches, fever, headaches, and fatigue (Homer et al.,), thus making diagnosis difficult. Anti-malarial drugs such as quinine and clindamycin are most effective in treatment of babesiosis (*Med. Lett. Drugs Ther.* 34(865):17-26 (1992)). Accordingly, accurate and early diagnosis of *B. microti* infection is critical.

Microscopy, PCR, indirect immunofluorescence assay, nucleic acid testing and ELISA-based tests are often used in diagnosing *B. microti* infection (Loa et al., *Current Microbiology* 49:385-389 (2004)). Microscopic and PCR analysis of blood samples may provide false-negative results when patients are first seen in the clinic. High throughput testing of serum samples from humans for *B. microti* are not suitable for nucleic acid testing. Because many of *B. microti*'s immunogenic epitopes are cross-reactive with other antibodies such as malaria (Houghton et al., *Transfusion* 42(11):1488-96 (2002)), ELISAs to detect antibodies of *B. microti* may not be effective due to unacceptable sensitivity and specificity, especially when antibodies to *B. microti* are at low titers. Accordingly, there remains a tremendous need to develop compositions in order to detect antibodies against *B. microti*.

SUMMARY

Provided herein is an agent that may be used to identify the presence of antibodies to *Babesia microti* (*B. microti*). The agent may comprise a plurality of peptides comprising a first group of peptides and an optional second group of peptides. Each peptide of the first group may comprise a peptide sequence selected from the group consisting of BMN1-17-4, BMN1-17-11, BMN1-17-12, MN10-3, MN10-5, MN10-6, MN 10-8 or a sequence at least 70% identical thereto. Each peptide of the first group may also comprise each of the sequences as set forth in SEQ ID NOS: 5-11 or a sequence at least 70% identical thereto.

The agent may be a chimeric protein comprising the plurality of peptides from the first group and optionally the second group. The chimeric protein may comprise the sequence as set forth in SEQ ID NO: 2. The agent may also be a fusion protein comprising a first portion and a second portion wherein the first portion is a chimeric protein comprising the plurality of peptides from the first group, and the second portion is a binding member. The fusion protein may comprise the sequence as set forth in SEQ ID NO: 4. The fusion protein may further comprise a third portion, wherein the third portion comprises a chimeric protein comprising the plurality of peptides.

A nucleic acid is also provided herein that encodes a plurality of peptides or one or more of these peptides. This plurality of peptides may comprise a first group of peptides and an optional second group of peptides. Each peptide of the first group may comprise a peptide sequence selected from the group consisting of BMN1-17-4, BMN1-17-11, BMN1-17-12, MN10-3, MN10-5, MN10-6, MN10-8 or a sequence at least 70% identical thereto. The nucleic acid may encode one or more peptides of the first group comprising a sequence as set forth in SEQ ID NOS: 5-11 or a sequence at least 70% identical thereto.

A nucleic acid may also encode a chimeric protein which may, in turn, comprise a plurality of peptides from the first group of peptides. The nucleic acid encoding the chimeric protein may comprise a sequence as set forth in SEQ ID NO: 1. A nucleic acid may also encode a fusion protein comprising a first portion and a second portion wherein the first portion is a chimeric protein comprising the plurality of peptides from the first group, and the second portion is a binding member. The nucleic acid encoding the fusion protein may comprise a sequence as set forth in SEQ ID NO: 3.

Vectors and host cells comprising the nucleic acids are also provided herein. An expression vector may comprise one or more of the nucleic acids described above and be operably linked to an expression or regulatory control sequence (e.g., a promoter).

A method of detecting antibodies to *B. microti* in a test sample is also described herein. The method may comprise contacting a sample with an agent as described above for a time and under conditions sufficient to form agent/antibody complexes, and detecting presence of the complexes, such presence indicating presence of antibodies to *B. microti* in the test sample. The method may comprise using a sample selected from the group consisting of blood, serum, plasma, salvia, cerebrospinal fluid, and urine. Further, the method may also comprise using an agent as described herein, wherein the agent is attached to a solid support, and wherein the solid support is selected from the group consisting of nitrocellulose, nylon, plastic, and paper.

The subject invention also encompasses another method of detecting antibodies to *B. microti* in a test sample. This method comprises the steps of contacting the test sample with an agent as described above for a time and under conditions sufficient to form agent/antibody complexes: adding a conjugate to the resulting agent/antibody complexes for a time and under conditions sufficient to allow the conjugate to bind to the bound antibody, wherein the conjugate comprises an anti-antibody attached to a signal-generating compound capable of generating a detectable signal; and detecting presence of antibody which may be present in the sample by detecting a signal generated by the signal-generating compound. The conjugate may comprise, for example, an anti-human IgG antibody, or a compound capable of binding the agent-anti-*B. microti* complex. The signal-generating compound may be a label.

Also provided herein is a method of diagnosing *B. microti* infection in a subject, comprising detecting presence of *B. microti* antibodies as described in the methods herein, and comparing the amount of anti-*B. microti* antibody to a control. A level of anti-*B. microti* antibody above the control may be indicative of *B. microti* infection.

BRIEF DESCRIPTION OF THE DRAWINGS

FIG. 2 shows an immunoblot strip. The *B. microti* recombinant chimeric protein comprising 7 peptides regions of BMN1-17-4, BMN1-17-11, BMN1-17-12, MN10-3, MN10-5, MN10-6, and MN10-8 is employed as a Test Band for detecting antibodies to *B. microti*. Three control bands, goat anti-human IgG ("Anti-hIgG"), hIgG-low ("hIgG-L"), and hIgG-high ("hIgG-H") are shown. Strip 1 is a negative control of human plasma antibodies non-specific for *B. microti* and is designated 99800, and shows three bands in the control section. Strip 2 is a negative control wherein the strip does not contain *B. microti* recombinant protein, but is probed with a human sample with *Babesia microti* antibodies. Strips 3-6 are four different human samples showing one test band specific to the *B. microti* recombinant chimeric protein comprising the amino acid sequences set forth in SEQ ID NOS: 5-11.

DETAILED DESCRIPTION

It has been discovered that certain peptides may be used to test for the presence of antibodies to *B. microti*. These peptides are selected based on the strength and specificity of the human antibody response to *B. microti*. These peptides alone or in combination have a variety of uses, for example, as a component of a diagnostic assay.

1. Definitions

The terminology used herein is for the purpose of describing particular embodiments only and is not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a. Alleles

"Alleles" are endogenous genes that may be altered as a result of one or more mutations, such as deletions, additions and/or substitutions of nucleotides.

b. Antibody

"Antibody" as used herein may mean an antibody of classes IgG, IgM, IgA, IgD or IgE, or fragments or derivatives thereof, including Fab, F(ab')2, Fd, and single chain antibodies, diabodies, bi-specific antibodies, bi-functional antibodies and derivatives thereof. The F(ab) and F(ab')$_2$ fragments may be generated by treating an antibody with an enzyme, such as pepsin. Light chains are classified as either kappa or lambda. The antibody may be a monoclonal antibody, polyclonal antibody, affinity-purified antibody, or fragments/mixtures thereof, which exhibit sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

c. Biological Sample

"Biological sample" or "test sample" or "control sample" as used herein may mean a sample derived from biological fluids, such as whole blood, serum, plasma, synovial fluid, cerebrospinal fluid, bronchial lavage, ascites fluid, bone marrow aspirate, pleural effusion, urine, as well as tumor tissue or any other bodily constituent or any tissue culture supernatant.

d. Epitope Tag

"Epitope Tag" as used in the context of a fusion protein may mean any moiety that may be used to identify, isolate or purify the protein. The epitope tag may be a human proto-oncogene c-myc, human influenza hemagglutinin protein (HA), histidine tag (His$_6$) (SEQ ID NO: 13), GFP (green flourescent protein), digoxigenin (DIG), biotin, or fluorescent dyes (FITC, Cy3, Cy5).

e. Hybridization Under Highly Stringent Conditions

"Hybridization under highly stringent hybridization conditions" as used herein may mean conditions under which a first nucleic acid sequence (e.g., probe) will hybridize to a second nucleic acid sequence (e.g., target), such as in a complex mixture of nucleic acids. Highly stringent conditions are sequence-dependent and will be different in different circumstances. Highly stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Highly stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Highly stringent conditions may also be achieved with the addition of destabilizing agents such as formamide. For selective or specific hybridization, a positive signal may be at least 2 to 10 times background hybridization. Exemplary highly stringent hybridization conditions include the following: 50% formamide, 5× SSC, and 1% SDS, incubating at 42° C., or, 5× SSC, 1% SDS, incubating at 65° C., with wash in 0.2× SSC, and 0.1% SDS at 65° C.

f. Hybridization Under Low Stringency Conditions

"Hybridization under low stringency conditions" as used herein may mean washing in a solution of 2-5× SSC at 50-55° C. Low stringency conditions may also comprise washing in 2× SSC, 0.1% SDS, at 50-55° C., or pre-washing and hybridization for 4 and 12 h, respectively, at 50° C. in 5× SSPE (0.2 M $NaH_2PO_4$, pH 7.4, 3M NaCl, 20 mM EDTA), which may contain 2.5× Denhardt's solution, 0.1% SDS, and 0.1 mg/ml denatured salmon sperm DNA.

g. Hybridization Under Moderately Stringent Conditions

"Hybridization under moderately stringent conditions" as used herein may mean pre-washing in a solution of 5× SSC, 0.5% SDS, 1.0 mM EDTA (pH 8.0); hybridizing at 50° C., or 65° C., 5× SSC, overnight; followed by washing twice at 65° C. for 20 minutes with each of 2×, 0.5× and 0.2× SSC containing 0.1% SDS. Hybridization techniques are well known in the art of molecular biology.

h. Identical Sequence

"Identical" as used herein may mean two sequences of nucleic acid or amino acids which are the same when aligned for maximum correspondence.

i. Linker Sequence

"Linker sequence" as used herein may mean a peptide sequence that connects two peptides of interest, acts as an enzyme cleavage site or has a physical and/or chemical property that can be used in the isolation or purification of a polypeptide.

j. Nucleic Acid Fragment

"Nucleic acid fragment" as used herein in reference to a nucleic acid may be employed at any length, with the total length being limited by the ease of preparation and use in the intended recombinant DNA protocol. Illustrative nucleic acid segments may be useful with total lengths of about 10,000, about 5000, about 3000, about 2,000, about 1,000, about 500, about 200, about 100, about 50 base pairs in length, and the like.

k. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. The promoter may comprise a T7, TP1, lactase, or metallothionein promoter.

l. Peptide

"Peptide" as used herein may mean at least two amino acids covalently linked together. As will be appreciated by those in the art, the depiction of an amino acid sequence also defines a single strand nucleic acid coding sequence and complementary strand.

m. Specific Binding

"Specific binding" as used herein may mean the preferential binding of binding partners to one another (e.g., two polypeptides, a polypeptide and nucleic acid molecule, or two nucleic acid molecules) at a specific site with a preference of at least 2-fold, 5-fold, 10-fold or 20-fold binding over a non-specific target molecule (e.g. a randomly generated molecule lacking the specifically recognized site(s)).

n. Substantially Complementary

"Substantially complementary" used herein may mean that a first sequence is at least 50%, 55%, 60%, 65%, 70%, 75%, 80%, 85%, 90%, 95%, 96%, 97%, 98%, or 99% identical to the complement of a second sequence over a region of 8, 9, 10, 20, 30, 40, 50, 60, 70, 80, 90, 100, 150, 200, 250, 300, 350 or more nucleotides or amino acids nucleotides, or amino acids. Intermediate lengths may mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. Substantial complementary may also mean that the two nucleotide sequences hybridize under stringent hybridization conditions using the methods described herein, (e.g., BLAST analysis using standard parameters, as described below)

o. Substantially Identical

"Substantially identical" used herein may mean that a first and second nucleotide or amino acid sequence are at least about 70%, 75%, 80%, 85%, 90%, 91%, 92%, 93%, 94%, 95%, 96%, 97%, 98%, or 99% identical over a region of 8, 9, 10, 20, 30, 40, 50, 60, 70, 80, 90, 100, 150, 200, 250, 300, 350 or more nucleotides or amino acids. Intermediate lengths may mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. Substantially identical may also mean the first sequence nucleotide or amino acid sequence is substantially complementary to the complement of the second sequence.

p. Variant

"Variant" as used herein in the context of a nucleic acid may mean a substantially identical or substantially complementary sequence. A variant in reference to a nucleic acid may further mean a nucleic acid that may contain one or more substitutions, additions, deletions, insertions, or may be fragments thereof. A variant may also be a nucleic acid capable of hybridizing under moderately stringent conditions and specifically binding to a nucleic acid encoding the agent. Hybridization techniques are well known in the art and may be conducted under moderately stringent conditions.

A variant in reference to a peptide may further mean differing from a native peptide in one or more substitutions, deletions, additions and/or insertions, or a sequence substantially identical to the native peptide sequence. The ability of a variant to react with antigen-specific antisera may be enhanced or unchanged, relative to the native protein, or may be diminished by less than 50%, or less than 20%, relative to the native peptide. Such variants may generally be identified by modifying one of the peptide sequences encoding an agent and evaluating the reactivity of the modified peptide with antigen-specific antibodies or antisera as described herein. Variants may include those in which one or more portions have been removed such as an N-terminal leader sequence or transmembrane domain. Other variants may include variants in which a small portion (e.g., 1-30 amino acids, or 5-15 amino acids) has been removed from the N- and/or C-terminal of the mature protein.

A variant in reference to a peptide may contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also contain nonconservative changes. Variant peptides differ from a native sequence by substitution, deletion or addition of five amino acids or fewer. Variants may also be modified by deletion or addition of amino acids, which have minimal influence on the immunogenicity, secondary structure and hydropathic nature of the polypeptide.

q. Vector

"Vector" as used herein may mean a nucleic acid molecule capable of transporting another nucleic acid to which it has been linked. The vector may be a plasmid, cosmid, bacteriophage, or viral vector. The vector may be capable of extrachromsosomal replication, such as an episome. The vector may be capable of directing expression of the nucleic acid to which it is operatively linked, such as an expression vector. Large numbers of suitable vectors and promoters are known to those of skill in the art and are commercially available. The following vectors are provided by way of example: bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223 3, pKK233 3, pDR540, pRIT5 (Pharmacia); and eukaryotic: pWLneo, pSV2cat, pOG44, pXT1, pSG (Stratagene) pSVK3, pBPV, pMSG, pSVL (Pharmacia).

2. Agent

An agent is provided that may be used to test for the presence of antibodies to *B. microti*. The agent may comprise a peptide. Also, the agent may comprise a plurality of peptides. The peptide may be synthesized or expressed (in vitro or in vivo) using a nucleic acid described herein.

The peptide may comprise an amino acid sequence as set forth in the table below and selected from the group consisting of BMN1-17-4, BMN1-17-11, BMN1-17-12, MN10-3, MN10-5, MN10-6, MN10-8, and BMN-MN or a variant thereof. The peptide may comprise an amino acid sequence as set forth in any of SEQ ID NOS: 2, 4, 5-11 or a variant thereof. The peptide may comprise an amino acid sequence isolated from other pathogenic organisms such as *Entamoeba histolytica, Giardia lamblia, Trypanosoma brucei, Toxoplasma gondii*, and Plasmodium. The peptide may have a length of 20-50 amino acids.

The plurality of peptides may comprise more than one of the same peptides or more than one of different peptides as described above. The plurality of peptides may comprise a first group and an optional second group of peptides. The first group of peptides may comprise an amino acid sequence as set forth in the table below and selected from the group consisting of BMN1-17-4, BMN1-17-11, BMN1-17-12, MN10-3, MN10-5, MN10-6, MN10-8, and BMN-MN or a variant thereof. The first group of peptides may comprise an amino acid sequence as set forth in any of SEQ ID NOS: 2, 4, 5-11, or a variant thereof. The first group of peptides may comprise an amino acid sequence isolated from other pathogenic organisms such as *Entamoeba histolytica, Giardia lamblia, Trypanosoma brucei, Toxoplasma gondii*, and Plasmodium. The optional second group of peptides may comprise may comprise an amino acid sequence as set forth in the table below and selected from the group consisting of BMN1-17-4, BMN1-17-11, BMN1-17-12, MN10-3, MN10-5, MN10-6, MN10-8, and BMN-MN or a variant thereof. The second group of peptides may comprise an amino acid sequence as set forth in any of SEQ ID NOS: 2, 4, 5-11, or a variant thereof. The second group of peptides may comprise an amino acid sequence isolated from other pathogenic organisms such as *Entamoeba histolytica, Giardia lamblia, Trypanosoma brucei, Toxoplasma gondii*, and Plasmodium.

TABLE 1

Peptides Used to ID Presence of Antibodies to *B. microti*

| Peptide | SEQ ID NO # | Amino Acid Sequence |
|---|---|---|
| BMNI-17-4 | SEQ ID NO:5 | GKPNTNKSEKAERKSHDTQTTQEICE |
| BMNI-17-11 | SEQ ID NO:6 | IKSYDTQTPQETSDAHEEEHGNLNK |
| BMN1-17-12 | SEQ ID NO:7 | GNLNKNKSGKAGIKSHNTQTPLKKK |
| MN10-3 | SEQ ID NO:8 | TCANTKFEALNDLIISDCEKKGIKIN |
| MN10-5 | SEQ ID NO:9 | YIVGAGVEAVTVSVSATSNGTESG |
| MN10-6 | SEQ ID NO:10 | TESGGAGSGTGTSVSATSTLTGNGG |
| MN10-8 | SEQ ID NO:11 | EAGGTSGTTTSSGAASGKAGTGTAG |
| BMN-MN | SEQ ID NO:12 | GKPNTNKSEKAERKSHDTQTTQEICE EAGGTSGTTTSSGAASGKAGTGTAG |

The agent may also comprise a chimeric protein, which may comprise at least one peptide or a plurality of peptides. The chimeric polypeptide may also comprise a linker sequence separating one or more of the plurality of peptides. The chimeric polypeptide may also comprise a binding member. The binding member may be an epitope tag.

The agent may also comprise a fusion protein, which may comprise the chimeric polypeptide, a peptide (as described above), a peptide variant or a plurality thereof. The fusion protein may also comprise a linker sequence separating the peptide from the chimeric peptide or polypeptide. The fusion protein may also comprise a binding member. The binding member may be an epitope tag as described above.

3. Nucleic Acid

Also provided herein is a nucleic acid that encodes the agent or a variant thereof. The nucleic acid may comprise a native sequence such as an endogenous sequence. The nucleic acid may also comprise SEQ ID NO: 1 or 3. The nucleic acid may be single stranded (coding or antisense) or double-stranded, and may be DNA (genomic, cDNA, or synthetic) or RNA molecules.

The nucleic acid may be combined with other DNA sequences, such as promoters, polyadenylation signals, polyhistidine signals additional restriction enzyme sites, multiple cloning sites, other coding segments, and the like. Nucleic acids may also be capable of hybridizing under moderately stringent conditions and specifically binding to a nucleic of an agent. Hybridization techniques are well known in the art of molecular biology. Suitable moderately stringent conditions for testing the hybridization of a nucleic acid with other nucleic acids may include pre-washing in a solution of 5× SSC, 0.5% SDS, 1.0 mM EDTA (pH 8.0); hybridizing at 50° C., or 65° C., 5× SSC, overnight; followed by washing twice at 65° C. for 20 minutes with each of 2×, 0.5× and 0.2× SSC containing 0.1% SDS.

As a result of the degeneracy of the genetic code, amino acid similarity, reading frame positioning and the like, there are many nucleic acid sequences that may encode the agent. Some of these nucleic acids may bear minimal homology to the nucleic acid sequence of any native *B. microti* gene. Nucleic acids of the agent may vary due to differences in codon usage. Further, alleles of the genes comprising the nucleic acid sequences of the agent within the scope of the present invention. The resulting mRNA and protein may, but need not, have an altered structure or function. Alleles may be identified using standard techniques (such as hybridization, amplification and/or database sequence comparison).

The nucleic acid may be used to synthesize or express (in vitro or in vivo) the agent. The nucleic acid may be cloned into a vector for recombinant expression as described below.

4. Vector

Also provided herein is a vector that comprises the nucleic acid. The vector may be an expression vector. The vector may comprise SEQ ID NO: 1 or 3. The vector may comprise a nucleic acid sequence or a plurality thereof encoding the amino acid sequences as set forth SEQ ID NOS: 5-11.

The expression vector may also include one or more control sequences capable of effecting and/or enhancing the expression of the agent. Control sequences that are suitable for expression in prokaryotes, for example, include a promoter sequence, an operator sequence, and a ribosome binding site. Control sequences for expression in eukaryotic cells may include a promoter, an enhancer, and a transcription termination sequence (i.e., a polyadenylation signal).

The expression vector may also include other sequences, such as, for example, nucleic acid sequences encoding a signal sequence or an amplifiable gene. A signal sequence may direct the secretion of a polypeptide fused thereto from a cell expressing the protein. In the expression vector, nucleic acid encoding a signal sequence may be linked to a polypeptide coding sequence so as to preserve the reading frame of the polypeptide coding sequence. The inclusion in a vector of a gene complementing an auxotrophic deficiency in the chosen host cell may allow for the selection of host cells transformed with the vector.

5. Host Cell/Expression of Agent

Also provided herein is a host cell that comprises the vector. A wide variety of host cells are available for propagation and/or expression of vectors. Examples include viruses (phage, DNA, RNA), prokaryotic cells (such as *E. coli* and strains of *Bacillus, Pseudomonas*, and other bacteria), yeast or other fungal cells (including *S. cerevesiae* and *P. pastoris*), insect cells, plant cells, as well as higher eukaryotic cells (such as human embryonic kidney cells and other mammalian cells).

A vector expressing the agent may be introduced into a host cell by any convenient method, which will vary depending on the vector-host system employed. Generally, a vector may be introduced into a host cell by transformation or infection (also known as "transfection") with a virus (e.g., phage) bearing the vector. If the host cell is a prokaryotic cell (or other cell having a cell wall), convenient transformation methods may include the calcium treatment method described by Cohen, et al. (1972) *Proc. Natl. Acad. Sci.*, USA, 69:2110-14. If a prokaryotic cell is used as the host and the vector is a phagemid vector, the vector may be introduced into the host cell by transfection. Yeast cells may be transformed using polyethylene glycol, for example, as taught by Hinnen (1978) *Proc. Natl. Acad. Sci, USA*, 75:1929-33. Mammalian cells are conveniently transformed using the calcium phosphate precipitation method described by Graham, et al. (1978) *Virology*, 52:546 and by Gorman, el al. (1990) *DNA and Prot. Eng. Tech.*, 2:3-10. However, other known methods for introducing DNA into host cells, such as nuclear injection, electroporation, protoplast fusion, and other means also are acceptable for use in the invention.

Expression of the agent from a transformed host cell may entail culturing the host cell under conditions suitable for cell growth and expression and recovering the expressed polypeptides from a cell lysate or, if the polypeptides are secreted, from the culture medium. In particular, the culture medium may contain appropriate nutrients and growth factors for the host cell employed. The nutrients and growth factors are, in many cases, well known or may be readily determined empirically by those skilled in the art. Suitable culture conditions for mammalian host cells, for instance, are described in Mammalian Cell Culture (Mather ed., Plenum Press 1984) and in Barnes and Sato (1980) *Cell* 22:649.

In addition, the culture conditions may allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolarity of the culture; and cell density. The adjustment of these factors to promote expression in a particular vector-host cell system is within the level of skill in the art. Principles and practical techniques for maximizing the productivity of in vitro mammalian cell cultures, for example, may be found in Mammalian Cell Biotechnology: a Practical Approach (Butler ed., IRL Press (1991).

Any of a number of well-known techniques for large- or small-scale production of proteins may be employed in expressing the agent. These may include the use of a shaken flask, a fluidized bed bioreactor, a roller bottle culture system, and a stirred tank bioreactor system. Cell culture may be carried out in a batch, fed-batch, or continuous mode.

Methods for recovery of the agent are well-known and vary depending on the expression system employed. An agent including a signal sequence may be recovered from the culture medium or the periplasm. The agent may also be expressed intracellularly and recovered from cell lysates.

The expressed agent may be purified from culture medium or a cell lysate by any method capable of separating the polypeptide from one or more components of the host cell or culture medium. The agent may be separated from host cell and/or culture medium components that would interfere with the intended use of the polypeptide. As a first step, the culture medium or cell lysate may be centrifuged or filtered to remove cellular debris. The supernatant may then typically concentrated or diluted to a desired volume or diafiltered into a suitable buffer to condition the preparation for further purification.

The agent may then be further purified using well-known techniques. The technique chosen will vary depending on the properties of the agent. For example, the agent may be purified using an affinity column containing the cognate binding partner of a binding member of the agent. For instance, the agent fused with green fluorescent protein, hemagglutinin, or FLAG epitope tags or with hexahistidine or similar metal affinity tags may be purified by fractionation on an affinity column.

6. Method of Detecting Antibodies to *B. microti*

A method is provided herein for detecting anti-*B. microti* antibodies in a test sample. The method may comprise contacting the agent with the test sample, and measuring the amount of anti-*B. microti* antibodies compared to a control sample.

An agent may be immobilized on a solid support. Also, the agent may be contacted with a blocking agent. Further, the agent may be contacted with a control sample or a test sample, which may comprise an anti-*B. microti* antibody. The agent may form an antigen-antibody complex with the anti-*B. microti* antibody, which may be contacted with a detection reagent. The detection reagent may comprise a detectable label. The method of detection may be included in a detection system.

a. Components of the Assay to Identify *B. microti* Antibodies (1) Solid Support A solid support may be used in a diagnostic assay to identify the presence of *B. microti* antibodies. The solid support may be any material known to those of ordinary skill in the art to which the agent may be attached. Examples of solid supports that may be used are a test well in a microtiter plate, nitrocellulose, nylon, a bead or a disc (which can be made out of glass, fiberglass, latex, plastic or a paper material), a gel (for example, a gel through which the polypeptides have been run and which is subsequently dried) or a strip, disc or sheet (which can be made out of nitrocellulose, nylon, plastic or paper). The support layer may be made from plastic, cardboard, etc. For example, a nitrocellulose strip or disc may be laminated onto a pressure-sensitive plastic film. The strip disc or sheet optionally comprises an identification region employed for labeling a sample such that it can be differentiated from other samples (e.g., name, number, alphanumeric reference, bar code, or other appropriate means) in addition to any discrete region employed for the location of an on-board control or test bands, spots or dots.

The agent may be bound to or immobilized on to the solid support using any techniques known to those skilled in the art (for example, using a Western blot technique, the method for which is well known to those skilled in the art). In addition, one or more controls may also be immobilized on to the solid support. The terms "bound" or "immobilized" as used interchangeably may refer to both the non-covalent association, such as adsorption, and covalent attachment (which may be a direct linkage between the recombinant protein) and the functional groups on the solid support or may be a linkage that is effected by way of a cross-linking agent). Adsorption to a strip, disc, or sheet may be achieved by contacting solutions of each of the recombinant polypeptides, and any control in a suitable buffer, with the strip, disc or sheet for a suitable amount of time. The contact time will vary depending on the temperature, but is between about 1 hour and about 24 hours.

The agent may be immobilized on said strip, disc or sheet. The agent may be arranged as separate, parallel bands, spots or dots on the strip, disc or sheet (each of which may be referred to as a "test" band, spot or dot, collectively as "test" bands, spots or dots). The agent may be immobilized on said strip, disc or sheet using routine techniques known in the art, such as automated techniques, such as by jetting the recombinant proteins on to said strip, disc or sheet (using a jetting instrument such as those available from Bio-Dot ((such as the AJQ3000 Air Jet Quanti or the RR 4200-Dip Tank), Irvine, Calif.) or manual techniques, such as by pipetting the recombinant proteins on to said strip, disc or sheet. If a sheet is used, once all of the recombinant proteins are immobilized onto the sheet, the sheet can be cut, using routine techniques known in the art into strips for use in an assay. The location of the agent (and optionally, any controls) on the strip, disc or sheet is not critical. Additionally, the strip, disc or sheet may be further immobilized on a support layer using routine techniques known in the art, such as gluing, lamination, etc.

If necessary, covalent attachment of the agent (and optionally, any controls) to a solid support may be achieved by first reacting the solid support with a bifunctional reagent that will react with both the support and a functional group, such as a hydroxyl or amino group, on the recombinant polypeptides. For example, the polypeptides may be bound to supports having an appropriate polymer coating using benzoquinone or by condensation of an aldehyde group on the support with an amine and an active hydrogen on the polypeptide.

(2) Blocking Reagent

Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), as well as other blocking reagent, may be employed. For use of a support comprising a gel, which is subsequently dried, blocking of the support may not be necessary. After blocking is completed, the support may be washed, such as with PBS and allowed to dry (such as by air drying) for a suitable amount of time. The drying time will vary depending on the temperature, but is between about 30 minutes and about 24 hours.

The immobilized agent (and optionally, one or more controls) is then allowed to incubate with the test sample. Prior to said incubation, the test sample may be diluted with a suitable diluent, such as PBS. During this incubation, if any antibodies are present in the test sample, these antibodies will bind to one or more of the recombinant polypeptides on the solid support. Generally, the incubation period is a period of time that is sufficient to permit the detection of the presence of *B. microti* antibodies within the test sample. The incubation period may be between about 15 minutes to about 6 hours. Preferably, the incubation period may be between about 1 hour and about 4 hours.

(3) Test Sample

The agent on the solid support may be contacted with a test sample. The test sample may contain an antibody to *B. microti*. The test sample may be isolated from a mammal including a human, a domestic mammal such as a dog, cat and hampster, or a wild mammal. The test sample may be blood, serum, plasma, saliva, cerebrospinal fluid, urine or other appropriate sample. The test sample may be serially diluted in buffer. For example, a serial dilution of a test sample may include a ratio of 1:64, 1:128, 1:256, 1:512, and 1:1024.

(4) Control Sample

The agent on the solid support may be contacted with a control sample. The control sample may be a positive control by containing an antibody to *B. microti*. The control sample may be a negative control by lacking antibodies to *B. microtis*. For example, the negative control sample may contain an antibody to Trypanosoma cruzi or designated Chagas SDB. A T. cruzi antibody may be reactive against a recombinant polypeptide selected from the group consisting of JL8, TCR27, JL7, TCR39, PEP-2, Ag36, JL9, TCNA, TcLo1.2, TS, TcD, FcaBP, Tc-28, Tc-40, FL-160, CEA, CRP, TcP2βN-C29, SA85-1.1, FP3, FP6, FP10, and TcF. The negative control may also comprise an antibody that does not bind peptides to *B. microti*. The control sample that is contacted with the agent may be isolated from mammals including humans, domestic animals such as dogs cats, and hampsters, and wild animals. The control sample from a mammal may be blood, serum, plasma, saliva, cerebrospinal fluid, urine or other appropriate sample. The control sample may be human plasma protein or immunoglobulins non-specific to *B. microti*. The control samples may be serially diluted in buffer. For example, a serial dilution of a control sample may be at ratios of 1:64, 1:128, 1:256, 1:512, and 1:1024.

(5) Detection Reagent

After blocking the agent, the agent may be contacted and detected using a detection reagent. Unbound test sample may be removed by washing the solid support with an appropriate buffer, such as PBS or a Tris buffer (such as a Tris buffer containing 20 mM Tris, 0.15% Tween 20™ and 0.1% sodium azide). The detectable reagent may be added to the solid support. Appropriate detectable reagents are any compounds that binds to the immobilized agent-antibody complex (and optionally any immobilized controls) and that can be detected by any of a variety of means that are known to those skilled in the art. The detectable reagent may contain a binding reagent, such as, for example, Protein A, Protein G, an immunoglobulin, a lectin or a free antigen) conjugated to a detectable label. The conjugation of the binding reagent to the detectable label may be achieved using standard methods known to those skilled in the art. Common binding reagent may be purchased conjugated to a variety of detectable labels from a number of commercial sources, such as Zymed Laboratories (San Francisco, Calif.) and Pierce (Rockford, Ill.).

The detection reagent may be incubated with the immobilized polypeptide-antibody complex (and optionally, one or more controls) for an amount of time that is sufficient to detect the bound antibody or antibodies (and optionally, one or more controls). A suitable incubation time may generally be determined from the manufacturer's instructions or by assaying the level of binding that occurs over a period of time. Unbound detection reagent may then be removed and bound detection reagent is detected using a detectable label. The method used for detecting the detectable label will depend on the nature of the detectable label used in the assay. For example, for a radioactive label, scintillation counting or autoradiographic methods can be used. For chemiluminescent or fluorescent labels, spectroscopic methods may be used. Enzymatic labels can generally be detected by the addition of a substrate (usually for a specific period of time), followed by spectroscopic or other analysis of the reaction products.

(6) Detection Labels

The detection reagent may comprise a detection label. The detectable label may be a radioactive label (such as, e.g., $^3$H, $^{125}$I, $^{35}$S, $^{14}$C, $^{32}$P, and $^{33}$P), an enzymatic label used for enzyme immunoassay (such as, e.g., horseradish peroxidase, alkaline peroxidase, glucose 6-phosphate dehydrogenase, luciferase and the like), a chemiluminescent label (such as, e.g., acridinium esters, luminal, isoluminol, thioesters, sulfonamides, phenanthridinium esters, and the like), a fluorescence label (such as, e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

Detectable labels may be measured by radioactive, colorimetric, or fluorescence imaging or other visual means. For example, the detection label can be measured in relative light units by a fluorescent imager.

b. Detection Systems (1) General Approach to Detecting *B. microti* Antibodies

The method of detecting described herein may be implemented in a variety of well-known detection systems to determine the presence of antibodies to *B. microti* in a test or control sample. Generally, the detection system may comprise a fluorescent or other means comparison between a signal generated from a detection label that is bound to the agent and a pre-determined value to determine the presence or absence of *B. microti* antibodies in the test sample. The pre-determined value may be a ratio of the signal measured from the test sample to the signal measured from the control sample. In general, a test sample generating a signal that is three standard deviations above the mean signal measured from a control sample that contains no *B. microti* antibodies may be considered positive for *B. microti* antibodies and *B. microti* infection.

Alternatively, an apparatus such as a densitometer may be employed for measuring a numerical value of the detectable label. The pre-determined value may be determined using a Receive Operator Curve ("ROC") using the method of Sackett el al., *Clinical Epidemiology: A Basic Science for Clinical Medicine*, p. 106-107 (Little Brown and Co., 1985). The pre-determined value may be based upon relative light units by a fluorescent imager or other means as describe above. Briefly, the pre-determined value may be determined from a plot of pairs of true positive rates (namely, sensitivity) and false positive rates (namely, 100% specificity) that correspond to each possible value for the diagnostic test result. The pre-determined value on the plot that is the closest to the upper left-hand corner (namely, the value that encloses the largest area) is the most accurate pre-determined value, and a sample generating a signal that is higher than the pre-determined value determined by this method may be considered positive. Alternatively, the pre-determined value may be shifted to the left along the plot, to minimize the false positive rate.

(2) Immunoblot

The method of detecting may be used in an immunoblot detection system to detect anti-*B. microti* antibodies. The immunoblot may use a solid support to immobilize the agent.

The immunoblot may use two separate control samples (namely, a first control and a second control), which may be immobilized on a solid support. The immunoblot may use three separate, discrete control samples (namely, a first control, a second control and a third control). If more than one control sample is present, then the controls may be identical to one another or different from one another. Two of the control samples may be identical (such as, for example, the first control and the second control). If two of the control samples are identical, the concentration of one of the control samples (either the first control or the second control or if three controls are present, the level of the first control or the third control or the second control or third control) may be higher (or greater) than the other control. The control sample may be in a higher concentration than the other control and may be referred to as the "high control". The control immobilized on the strip, disc or sheet in a lower concentration than the high control may be referred to as the "low control". The ratio of the concentration of low control to high control may be from about 1:2 to about 1:10, preferably, about 1:5 to about 1:6. For example, the first control may be the low control and the second control may be the high control. Alternatively, the first control may be the high control and the second control may be the low control. By way of another example, a three control detection system may comprise a low control and a high control as well a third control (which can be used, for example, to verify sample addition). The low control and high control may be human plasma (wherein the ratio of low control to high control is from about 1:2 to about 1:10) and the third control may be SDB Chagas or human plasma.

In the flow-through format, an immobilized agent on the solid support may be immersed in a solution containing the test sample. Alternatively, the solid support may be placed in a reaction tray along with a diluent and then the test sample added to the reaction tray. The test sample and agent are allowed to incubate for a sufficient period of time using the same times and techniques described previously herein. Unbound test sample may be removed using the techniques described previously herein. In this format, anti-*B. microti* antibodies within the test sample may bind to the immobilized agent (and the at least one control) as the test sample passes through the membrane. At least one detection reagent (such as a detection reagent described previously herein containing a detectable label) may be added. At least one detection reagent may bind to each of the agent-antibody complexes formed as the solution containing the detection reagent flows through the strip. To determine the presence or absence of *B. microti* antibodies in the test sample, the detection of the bound detection reagents may be performed as described above using the a cut-off or by comparing the intensity of one or more signals generated by one or more controls as discussed in more detail below.

When a low control and high control as described above may be used in the flow-through format, the presence or absence of the *B. microti* antibodies in the test sample may be determined by identifying the presence of a signal from the detectable label at each of the test bands (or spots or dots) for the agents. If a signal is identified at a test band for a agent, then the intensity of this detected signal is compared with the intensity of the signal from the low control band (or spot or dot) and the high control band (or spot or dot), using a scale of 0 to 4+. The reading is 0 when no band is visible. The intensities of the low control band and high control band may be defined as 1+ (for the low control) and 3+ (for the high control), respectively. A test band with an intensity comparable to that of the low control would be rated 1+. A band with intensity between that of the low control and the high control band would be rated 2+. A band with an intensity comparable to that of the high control would be rated 3+. A band intensity higher than that of the high control would be rated 4+. A faint band with intensity weaker than that of the low control would be rated +/− (See Table 2). As shown in the exemplary algorithm described in FIG. 2 of U.S. patent appl. Ser. No. 11/583, 203, and incorporated fully by reference, immunoblot assays can provide a visual indication of whether the test sample is positive or negative for anti-*B. microti* antibodies.

TABLE 2

| Intensity | Score |
| --- | --- |
| Absent | 0 |
| Faint or < on-board hIgG-L CTL | +/− |
| = on-board hIgG-L CTL | 1+ |
| Between on-board hIgG-L CTL and hIgG-H CTL | 2+ |
| = on-board hIgG-H CTL | 3+ |
| > on-board hIgG-H CTL | 4+ |

(3) Competitive Assay

The method of detecting may be used in a competitive detection system to identify test samples with antibodies specific for *B. microti*. The agent may be immobilized on a solid support as described above. The immobilized agent may then be contacted with a competitive antibody that is detectable labeled, known to bind the agent, and competes with anti-*B. microti* antibodies in the test sample. The immobilized agent is also contacted with the test sample. The signal from the detectably labeled antibody may be lower in test samples containing antibodies specific for *B. microti* because both sets of antibodies are competing for the immobilized agent.

Of course, it goes without saying that any of the exemplary formats herein, and any assay or kit according to the invention, can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063, 081 and published U.S. Patent Applications 20030170881, 20040018577, 20050054078, and 20060160164 (incorporated by reference herein for their teachings regarding same).

7. Diagnostic Kit

The invention also provides test kits for assaying samples for antibodies to *B. microti*. Test kits according to the invention include one or more reagents such as the agent useful for practicing one or more immunoassays according to the invention. A test kit generally includes a package with one or more containers holding the reagents, as one or more separate compositions or, optionally, as admixture where the compatibility of the reagents will allow. The test kit may also include other material(s), which may be desirable from a user standpoint, such as a buffer(s), a diluent(s), a standard(s), and/or any other material useful in sample processing, washing, or conducting any other step of the assay.

In certain embodiments, a test kit includes a humanized monoclonal antibody, wherein the humanized monoclonal antibody is specific for the agent. This component may be used as a positive control in immunoassays according to the invention. If desired, this component may be included in the test kit in multiple concentrations to facilitate the generation of a standard curve to which the signal detected in the test sample may be compared. Alternatively, a standard curve may be generated by preparing dilutions of a single humanized monoclonal antibody solution that is provided in the kit.

Kits according to the invention may include a solid phase and an agent affixed to a solid support. Kits may be employed for conducting sandwich immunoassays, and include a labeled detection antibody. The labeled detection antibody may be an anti-human IgG labeled antibody. The kit may further include a detectable label.

In certain embodiments, the test kit may include at least one direct label, such as acridinium-9-carboxamide. Test kits according to the invention may also include at least one indirect label. If the label employed generally requires an indicator reagent to produce a detectable signal, the test kit may include one or more suitable indicator reagents.

The kit may include a solid phase. Test kits according to the invention may include instructions for carrying out one or more of the immunoassays of the invention. Instructions included in kits of the invention may be affixed to packaging material or may be included as a package insert. While the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

EXAMPLE 1

Peptide-Coated Microparticles

The following results indicate that *Babesia* seroreactivity can be measured from serum of *Babesia*-infected subjects using *Babesia* antigens bound to microparticles. To generate peptide-coated microparticles, *Babesia* antigens MN-10-8 (SEQ ID NO: 11) and BMN1-17-4 (SEQ ID NO: 5) were synthesized using Fmoc (i.e., 9-fluorenylmethyl carbamate) chemistry according to methods well known in the art, such as described in Houghton R L, et al., *Transfusion*, 2002; 42:1488-96, the contents of which are incorporated herein by reference. A peptide consisting of the combined MN-10-8 and BMN1-17-4 antigens, BMN-MN (SEQ ID NO: 12) was similarly produced. The *Babesia* antigens were immobilized on microparticles according to methods well-known in the art, such as those described in U.S. Publication No. 20040023865, the contents of which are incorporated herein by reference.

The *Babesia* peptide-coated microparticles (0.05% solid) were blocked, and then incubated with one of five different serum samples from subjects with known *B. microti* infection, or with human plasma negative control (NC). The negative controls were performed in quadruplicate. After incubation, the microparticles were washed. Next, 25 ng/mL of mouse-anti-human IgG conjugated to a bioluminescent enzyme, washed, and then incubated with a substrate capable of triggering bioluminescence was added, washed, and then incubated with a substrate capable of triggering bioluminescence. The amount of luminescence was then measured in relative light units (RLU) using a bioluminescence imager. The positive-to-negative control (P/N) ratio was measured by dividing the RLU measurement for each *Babesia*-infected sample by the average RLU value of the four negative controls. The results are shown in Table 3.

TABLE 3

| | MN-10-8 | | BMN1-17-4 | | BMN-MN |
|---|---|---|---|---|---|
| Sample | P/N | Mean NC | P/N | Mean NC | P/N |
| 1 | 0.84 | 221.75 | 1.15 | 168.75 | 0.98 |
| 2 | 0.72 | 221.75 | 0.93 | 168.75 | 0.86 |
| 3 | 1.76 | 251.25 | 9.38 | 253.25 | 6.49 |
| 4 | 1.15 | 221.75 | 5.52 | 168.75 | 8.39 |
| 5 | 2.15 | 251.25 | 9.01 | 253.25 | 9.05 |

Microparticles coated with *Babesia* antigens MN-10-8, BMN1-17-4, and BMN-MN at a concentration of 2.5 µg/L were also tested for seroreactivity to *Babesia*-infected serum in EIA as follows. The microparticles were blocked, washed and then incubated with one of five *Babesia*-infected serum samples (each sample in duplicate), negative control (99800), or malaria-infected serum (SDB). Next, after washing the microparticles, seroreactivity was measured using reagents from HCV EIA 2.0 (Abbott Laboratories, Abbott Park, Ill.) according to the manufacturer's protocol. The results are shown in Table 4.

TABLE 4

| | MN-10-8 | | | BMN1-17-4 | | | BMN-MN | | |
|---|---|---|---|---|---|---|---|---|---|
| Sample | OD492 | Mean | P/N | OD492 | Mean | P/N | OD492 | Mean | P/N |
| SDB | 0.003 | | | 0.004 | | | 0.007 | | |
| | 0.004 | | | 0.006 | | | 0.038 | | |
| | 0.006 | | | 0.004 | | | 0.005 | | |
| 99800 | 0.015 | 0.016 | | 0.01 | 0.0095 | | 0.012 | 0.012 | |
| | 0.017 | | | 0.009 | | | | | |
| 1 | 0.02 | 0.015 | 0.94 | 0.008 | 0.0105 | 1.11 | 0.024 | 0.0245 | 2.04 |
| | 0.01 | | | 0.013 | | | 0.025 | | |
| 2 | 0.013 | 0.0145 | 0.91 | 0.015 | 0.0135 | 1.42 | 0.01 | 0.016 | 1.33 |
| | 0.016 | | | 0.012 | | | 0.022 | | |
| 3 | 0.015 | 0.015 | 0.94 | 0.164 | 0.1905 | 20.05 | 0.171 | 0.182 | 15.17 |
| | 0.015 | | | 0.217 | | | 0.193 | | |
| 4 | 0.016 | 0.0235 | 1.47 | 0.177 | 0.161 | 16.95 | 0.13 | 0.13 | 10.83 |
| | 0.031 | | | 0.145 | | | | | |
| 5 | 0.01 | 0.0125 | 0.78 | 0.832 | 0.994 | 104.63 | 0.525 | 0.5185 | 43.21 |
| | 0.015 | | | 1.156 | | | 0.512 | | |

These results indicate that microparticles coated with *Babesia* antigens can be used to measure seroreactivity to *Babesia* antibodies in serum from subjects.

EXAMPLE 2

Chimeric Protein for Detecting Seroreactive Antibodies

The following describes a synthetic chimeric recombinant protein (the "Chimeric Protein") including seven *Babesia* peptides that were selected by virtue of their relatively strong seroreactivity and specificity. The following selection criteria were used: mean $OD_{450} \geqq 0.1$, mean $OD_{450}$ for malaria-infected serum approximately $\leqq 60\%$ compared to *Babesia*-infected serum, and mean $OD_{450}$ for negative control approximately $\leqq 60\%$ compared to *Babesia*-infected serum. The DNA sequence encoding this chimeric protein (the "Chimeric Sequence," FIG. 1) was designed with EcoRI and BamHI sites at the 5'- and 3'-ends, respectively. These sites were used for cloning into the same sites in expression vector pKRR826 (a pL-based vector that generates a non-fusion product), and could likewise be used for cloning into pJO200 (a vector generating a CKS-fusion product). The DNA sequence contains no other internal EcoRI or BamHI sites.

To generate the expression construct, a start codon was inserted in-frame immediately upstream of the Chimeric Sequence such that it was positioned at the optimal distance downstream (typically 12 to 14 bases) from the start of the vector Shine Dalgarno sequence. The Chimeric Sequence was codon-optimized as much as possible for expression in *E. coli*. No rare codons were used. An *E. coli* codon usage table from Henaut and Danchin: Analysis and Predictions from *Escherichia coli* Sequences, *Escherichia* and *Salmonella*, Vol. 2, Ch. 114:2047-2066, 1996, Neidhardt F C ed., ASM Press, Washington, D.C. was used for codon selection. The sense strand was scanned for potential Shine Dalgarno consensus sequences (i.e., 5' UAAGGAG), which could result in undesired ribosome loading and reduced expression of the Chimeric Protein. Any strong consensus matches were changed to an alternative codon. There were no perfect matches with the most conserved 4 base core sequence (AGGA). Several sites matched at 5 out of 7 positions, and at least one, if not both, mismatches were at more highly conserved positions.

The Chimeric Sequence was also searched for potential transcription termination sites (i.e., a modest stem-loop structure on the sense strand in which a GC-rich stem was preceded by a C within 2 bases upstream and followed by a T-rich stretch immediately downstream), which could result in expression of a truncated product. None was found.

Through alternative codon use, significant palindromes were broken up, especially when they were present at or near the ends of the synthetic oligonucleotides to be used in assembling the expression construct. Through alternative codon use, complementarity between the 5' or 3' end of the synthetic oligonucleotides of the Chimeric Sequence to undesired sequences within the construct was minimized to reduce the chance of incorrect priming during assembly. Adjacent oligonucleotides contained 20 base terminal overlaps to facilitate extension/PCR assembly of the Chimeric Sequence prior to cloning. The Chimeric Sequence was also searched for the presence of the acid labile peptide pair Asp-Pro. None was found.

A di-peptide consisting of Ala and/or Gly was inserted between peptide segments of the Chimeric Protein to serve as a flexible spacer. This was not done when the peptides were derived from normally overlapping adjacent sequences, or if a spacer of this type was already present.

Figure 1:
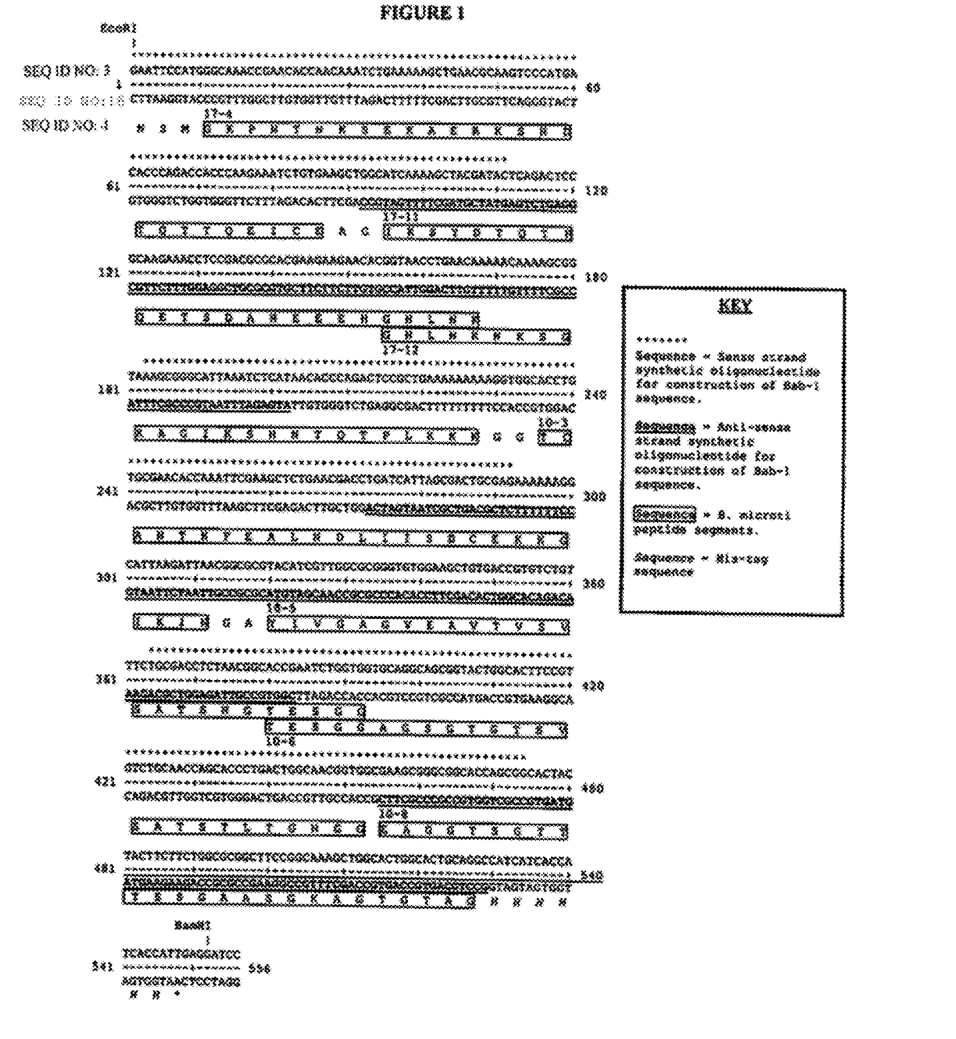
FIG. 1 shows a single chimeric construct insert containing seven peptides (full length anti-sense nucleotide sequence identified as SEQ ID NO: 16) from two different *B. microtiti* proteins (i.e., BMN1-17-4 (SR) ID NO:5), BMN1-17-11 (SEQ ID NO:6), BMN1-17-12 (SEQ ID NO:7), MN10-3 (SEQ ID NO:8), MN10-5 (SEQ ID NO:9), MN10-6 (SEQ ID NO:10), and MN10-8 SEQ ID NO:11)) based on the strength and specificity of the human antibody response following *B. microtiti* infection (full length nucleotide disclosed as SEQ ID NO: 3: full-length protein construct identified as SEQ ID NO: 4). Amino acid sequences enclosed by a box are the *B. microtiti* peptide segments. From the 5' end, the sequence of the Bab-1 sequence encodes the amino acid sequence of BMN1-17-4, followed by BMN1-17-11, wherein the last five amino acids (GNLNK (SEQ ID NO:14)) of BMN1-17-11 overlap with the first five amino acids of BMN1-17-12. *B. microtiti* amino acid sequence MN10-3 follows BMN1-17-12, and MN10-5 follows MN10-3. The last five amino acids of MN10-5 (i.e., TESGG (SEQ ID NO:15)) overlap with the first five amino acids of MN10-6. *B. microtiti* amino acid sequence MN10-8 follows MN10-6. A His-tag sequence is located at the 3' end of the chimeric protein.

A stop codon was located at the end of the chimeric ORF for translation termination, and a His-tag peptide sequence was added after the last of the Chimeric Sequence and before the stop codon. The Chimeric Protein was successfully expressed from the Chimeric Sequence expression construct, and then purified and used in serological identification. A schematic of the Chimeric Sequence and Chimeric Protein are shown in FIG. 1.

EXAMPLE 3

Seroreactivity to the Chimeric Protein

Figure 2:
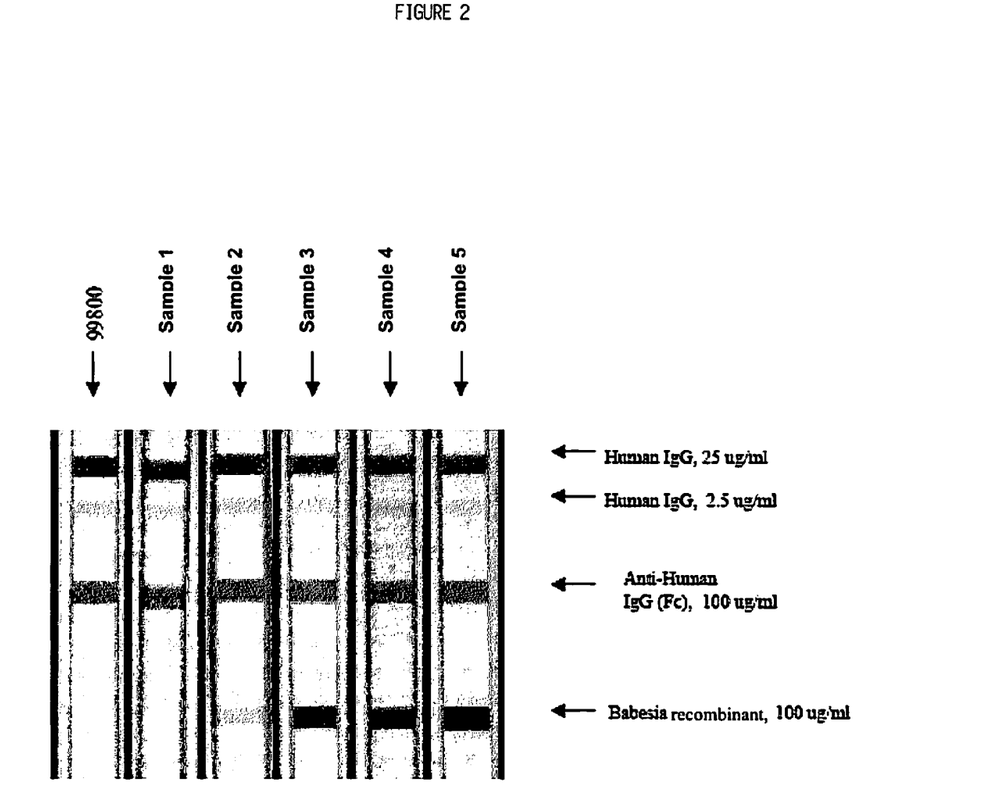

The following results demonstrate that the Chimeric Protein of Example 2 shows seroreactivity to serum from a *Babesia*-infected subject. The results, as measured by strip testing and described below, are depicted in FIG. 2.

Immunostrips were prepared using control solutions of human IgG-high concentration (25 µg/mL), human IgG-low concentration (2.5 µg/mL), and goat anti-human IgG (100 µg/mL), as well as the Chimeric Protein (100 µg/mL). Specifically, each protein was dissolved in a pH 7, 50 mM sodium 3-(N-morpholino)-2-hydroxypropanesulfonate buffer. Using a microprocessor controlled XYZ3050 dispensing system from Bio-Dot (Irvine, Calif.) 100 µL of each protein sample was jetted on to nitrocellulose membrane sheets (0.45 micron, 2×3 in; Whatman Schleicher & Schell, Keene, N.H.) in parallel lines in the relative positions depicted in FIG. 2 and incubated for 1 hr at room temperature (RT). The concentrations of the jetting solutions were as described above. After incubation, the membrane was washed with 100 mL phospho-buffered saline (PBS), blocked with 5% non-fat dried milk in PBS for 30 min at RT, washed for 5 min in 100 mL PBS three times, and air-dried. As a final step, the membrane sheet was laminated with a pressure sensitive plastic film and cut into 3 mm wide strips.

Both negative control and five *Babesia*-infected specimens were tested via the above immunostrip as follows. The negative control (99800, FIG. 2) was recalcified normal human plasma that tested negative in assays for the hepatitis B surface antigen ("HBsAg") and for antibodies to the core protein of hepatitis B virus ("HBcore"), hepatitis C virus ("HCV"), human immunodeficiency virus ("HIV") and human T-cell lymphotrophic virus ("HTLV"). The *Babesia* antibody positive specimens (samples 1-5, FIG. 2) were isolated from blood drawn from donors with confirmed *Babesia* infection.

Previously frozen serum or plasma samples were microfuged (14,000 rpm, 5 minutes) in 1.5-ml Eppendorf tubes prior to testing to remove particulate matter; samples that had never been frozen were not centrifuged. 3 mL of diluent and an immunostrip were placed in each trough of an immunoblot reaction tray (Bio-Rad, Hercules, Calif.) and incubated for 5 min at RT. During each incubation step, the contents of the troughs were gently mixed on a rocker. A 50 µL sample was added to each well containing a strip in diluent and incubated for 2 hours at RT, followed by aspiration, rinsing in TNT buffer (pH 8.0, 20 mM Tris, 0.5 M NaCl, 0.3% Tween-20), and three washes with 5 mL TNT buffer at RT. Next, 3 mL of a 0.2 µg/mL alkaline phosphatase conjugated goat anti-hIgG solution were added to each trough, and incubated for 1 h at RT. Wells were aspirated and strips were washed three times with 5 mL TNT buffer for 5 min at RT. Following this, 2 ml of a substrate solution of 5-bromo-4-chloro-3-indolylphosphate/nitro blue tetrazolium ("BCIP/NBT"; 1 tablet in 20 ml distilled water; Sigma-Aldrich, St. Louis, Mo.) was added to each well and incubated at ambient temperature for 10 minutes at RT for color development. This was followed by aspiration and three washes with distilled water to stop color development. Subsequently, the strips were removed from the troughs and air dried for reading via an AlphaImager System. The total assay time was about 4 hours.

FIG. 2 indicates that while the negative control showed no reactivity to the Chimeric Protein, Samples 2-5 each showed seroreactivity to the Chimeric Protein. Hence, the Chimeric Protein can be used to measure the presence of antibody in the blood of a subject infected with *Babesia*.

The invention claimed is:

1. An agent selected from the group consisting of the following:
   (a) a first peptide and an optional second peptide, wherein said first peptide consists of a sequence as set forth in SEQ ID NO:7;
   (b) a chimeric protein consisting of said first peptide and a second peptide; and
   (c) a fusion protein consisting of a first portion and a second portion, wherein the first portion is a protein according to
   (b) and the second portion is a binding member.

2. An agent comprising a chimeric protein, wherein said chimeric protein comprises a first peptide and a second peptide, and wherein said chimeric protein comprises the sequence of SEQ ID NO: 2.

3. An agent comprising a fusion protein, wherein said fusion protein comprises a first and a second portion, wherein said first portion is a chimeric protein comprising a first peptide and a second peptide and said second portion is a binding member, and wherein said fusion protein comprises the sequence of SEQ ID NO: 4.

4. A method of detecting the presence of antibodies to B. microti in a test sample comprising the steps of
   (a) contacting said test sample with an agent according to claim 1 for a time and under conditions sufficient to form agent/antibody complexes; and
   (b) detecting the presence of said agent/antibody complexes, presence of said complexes indicating presence of antibodies to B. microti in said test sample.

5. The method of claim 4, wherein said test sample is selected from the group consisting of blood, serum, plasma, saliva, cerebrospinal fluid and urine.

6. The method of claim 4, wherein the agent is attached to a solid support.

7. A method of diagnosing B. microti injection in a subject comprising the steps of:
   (a) detecting the presence of antibodies to B. microti in a test sample according to the method of claim 4; and
   (b) comparing the amount of anti-B. microti antibody to a control, wherein a level of anti-B. microti antibody above the control is indicative of B. microti infection.

8. A method of detecting antibodies to B. microti in a test sample comprising the steps of:
   (a) contacting said test sample with an agent according to claim 1 for a time and under conditions sufficient to form agent/antibody complexes:
   (b) adding a conjugate to the resulting agent/antibody complexes for a time and under conditions sufficient to allow said conjugate to bind to the bound antibody, wherein said conjugate comprises an anti-antibody attached to a signal-generating compound capable of generating a detectable signal; and (c) detecting presence of antibody which may be present in said sample by detecting a signal generated by said signal-generating compound, presence of said signal indicating the presence of antibodies to *B. microti* in said test sample.

9. The method of claim 8, wherein said test sample is selected from the group consisting of blood, serum, plasma, saliva, cerebrospinal fluid and urine.

10. The method of claim 8, wherein the agent is attached to a solid support.

11. A method of diagnosing *B. microti* injection in a subject comprising the steps of:

(a) detecting the presence of antibodies to *B. microti* in a test sample according to the method of claim 8; and (b) comparing the amount of anti-*B. microti* antibody to a control, wherein a level of anti-*B microti* antibody above the control is indicative of *B. microti* infection in said subject.

* * * * *